United States Patent [19]

Walker

[11] Patent Number: 4,568,492

[45] Date of Patent: Feb. 4, 1986

[54] Δ16-20-KETO STEROID CONVERSION TO 17α-HYDROXY-20-KETO STEROIDS

[75] Inventor: Jerry A. Walker, Kalamazoo, Mich.

[73] Assignee: The Upjohn Company, Kalamazoo, Mich.

[21] Appl. No.: 650,967

[22] Filed: Sep. 14, 1984

[51] Int. Cl.[4] ............................................. C07J 71/00
[52] U.S. Cl. ..................... 260/239.55 R; 260/397.45
[58] Field of Search ....................... 260/397.45, 239.55

[56] References Cited

U.S. PATENT DOCUMENTS

| | | | |
|---|---|---|---|
| 2,864,834 | 12/1958 | Mendelsohn et al. | 260/397.45 |
| 3,461,144 | 8/1969 | Taub et al. | 260/397.45 |
| 3,493,563 | 2/1970 | Diassi | 260/239.55 |
| 4,500,461 | 2/1985 | Van Rheenen | 260/397.45 |

OTHER PUBLICATIONS

Journ. Am. Chem. Soc., 78, 5693-5694 (1956), "16-Hydroxylated Steroids . . . " Bernstein et al.
Journ. Am. Chem. Soc., 82, 3399-3404 (1960), "Steroids. CXXXVII.[1] Synthesis of a New Class of Potent Cortical Hormones . . . " J. S. Mills et al.
Helv. Chim. Acta, 61, 3068-3071 (1978), "Herstellung von Cortexon-Analogen mit konformativ . . . " P. Wieland.
Journ. of Organometallic Chem., 94, 449-461 (1975), "Reduction of Carbonyl Compounds via Hydrosilylation" Ojima et al.
Tetrahedron Letters No. 49-50, 4319-4322 (1974), "Peracid Oxidation of Trimethylsilyl enol Ethers . . . " G. M. Rubottom et al.

*Primary Examiner*—Elbert L. Roberts
*Attorney, Agent, or Firm*—Bruce Stein

[57] ABSTRACT

Δ16-20-keto steroids (I) are converted to 17α-hydroxy-20-keto steroids (III) in 2 steps, hydrosilylation followed by peracid oxidation.

20 Claims, No Drawings

Δ16-20-KETO STEROID CONVERSION TO 17α-HYDROXY-20-KETO STEROIDS

BACKGROUND OF THE INVENTION $\Delta^{16}$-20-keto steroids have been converted to 16-substituted 20-keto steroids as is well known to those skilled in the art. More particularly, $\Delta^{16}$-20-keto steroids have been converted to 16α-methyl-17α-hydroxy-20-keto steroids (U.S. Pat. Nos. 3,461,144) and 16α,17α-dihydroxy-20-keto steroids (U.S. Pat. Nos. 3,493,563 and 2,864,834 and J. Am. Chem. Soc. 78, 5693 (1956) and J. Am. Chem. Soc. 82, 3399 (1960)).

The transformation of a $\Delta^{5,16}$-20-keto steroid to the corresponding 20-trimethylsilylenol ether by hydrosilylation is described in Helv. Chem. Acta 61, 3068 (1978).

The hydrosilylation of enones with silanes in the presence of tris-(triphenylphosphine)rhodium (I) chloride catalyst is known where there is 1,4-addition of the silane to the α,β-unsaturated carboxy compound; see J. Organometallic Chemistry 94, 449 (1975).

The oxidation of non-steroid silylenol ethers to the corresponding α-hydroxy ketones is discussed in Tetrahedron Letters 4319 (1974).

SUMMARY OF THE INVENTION

Disclosed is a $\Delta^{17(20)}$-20-silyl ether (II A-B).

Also disclosed is a process for the preparation of a 17α-hydroxy-20-keto steroid (III) which comprises (1) contacting a $\Delta^{16}$-20-keto steroid (I) with a silylating agent of the formula R'R"R'''SiH in the presence of a transition metal catalyst to give a $\Delta^{17(20)}$-20-silyl steroid (II) and (2) contacting the $\Delta^{17(20)}$-20-silyl steroid (II) with a peracid.

DETAILED DESCRIPTION OF THE INVENTION

The $\Delta^{16}$-20-keto steroid (I A-B) starting materials are well known to those skilled in the art or can be readily prepared from known steroids by methods well known to those skilled in the art; see for example, U.S. Pat. No. 4,216,159 and J. Am. Chem. Soc. 77, 1028 (1955).

With the $\Delta^4$-3-keto (A) and $\Delta^{1,4}$-3-keto steroids (B) the $C_3$ ketone does not have to be protected because the hydrosilylation takes place preferentially at $C_{20}$ over $C_3$.

The $\Delta^{16}$-20-keto steroid (I) is reacted with a silane reagent in the presence of a transition metal catalyst.

The 1,4-reduction of enones with silanes catalyzed by various transition metals is well known to those skilled in the art. See, for example, Y. Nagai, Org. Prep. Proced. Int. 12, 15 (1980) at p 25; Y. Nagai, Bull. Chem. Soc. Jap. 45, 3506 (1972); Y. Nagai, Tet. Letters 5085 (1972); Lutsenko, J. Organometal. Chem. Rev. Sect. A, 6, 355 (1970) at p 382-383; and Y. Nagai, J. Organometal Chem., 94, 449 (1975).

The reaction is performed by contacting the enone ($\Delta^{16}$-20-keto steroid) with a silane (R'R"R'''SiH) in a suitable solvent with a transition metal catalyst. Numerous silanes are operable as defined by R', R" and R'''. The preferred silanes are trimethyl, triethyl, dimethylmethoxy, diethoxymethyl, ethoxydimethyl, tetramethyldisiloxane, and more preferred is triethylsilane.

Numerous transition metal catalysts are operable including salts and complexes of platinum (Pt), palladium (Pd), rhodium (Rh), ruthenium (Ru), cobalt (Co) and nickel (Ni). For example, for platinum: $H_2PtCl_6 \cdot H_2O$, $(\phi_3P)_2PtCl_2$, Pt(O) on supports; for palladium (II): $PdCl_2$, $(\phi_3P)_4Pd$, $(\phi_3P)_2PdCl_2$; for ruthenium (III): $(\phi_3P)_3RuCl_2$; for rhodium (I): $(\phi_3P)_3RhCl$, $(\phi_3P)_2Rh(CO)Cl$, $(\phi_3P)_3Rh(CO)H$, $[RhCl(CO)_2]_2$, $[(C_2H_4)_2RhCl]_2$; for cobalt: $Co_2(CO)_8$, $HCo(CO)_4$, $(\phi_3P)_3CoH_3$ and for nickel: $(\phi_3P)_3NiCl_2$, $Ni(CO)_4$, $[Ni(COD)_2]$. Preferred are $(\phi_3P)_3RhCl$, $(\phi_3P)_3Rh(CO)H$, $(\phi_3P)Rh(CO)Cl$, $[RhCl(CO)_2]_2$ and $[(C_2H_4)_2RhCl]_2$. Most preferred is tris(triphenylphosphine)rhodium (I) chloride, $(\phi_3P)_3RhCl$.

The reaction is performed by contacting a $\Delta^{16}$-20-keto steroid (I) with at least one equivalent of a silane of the formula R'R"R'''SiH in a suitable solvent with an effective amount of a transition metal catalyst. Solvents including hydrocarbons, chlorinated hydrocarbons, aromatics, ethers, esters and mixtures thereof are operable. Preferred solvents include methylene chloride, ethylene dichloride, benzene, toluene, xylene, THF, dimethoxyethane, ethylacetate and butylacetate.

The amount of transition metal catalyst is not critical, but must be sufficient to effectuate the reaction in a reasonable amount of time. For $(\phi_3P)_3RhCl$ usually 0.1% (mole) is effective.

The reaction is generally performed in the temperature range of about 0° to about 150°, preferably from about 20° to about 100° and requires about 0.5 to several hours to complete.

The reaction is quite specific and does not interfere with many typical steroid functional groups. Olefins such as $\Delta^{9(11)}$ or $\Delta^{14(15)}$ can be present. The α/β-unsaturated ketone ($\Delta^4$-3-keto) is unreactive under conditions where the $\Delta^{16}$-20-ketone will react. Acetoxy groups at $C_{11}$ and/or $C_{21}$ can be present. If free alcohol groups at $C_{11}$, or $C_{21}$ are present, they may be silated under the reaction conditions. Hence, an additional equivalent of silating agent may be required for each free hydroxyl group. Since the silating agent is relatively expensive, it may be preferred to protect the free hydroxyl groups during the silylation reaction as is well known to those skilled in the art. Suitable protecting groups include ester ($R_{21}$ is —$COR_{21}\alpha$) or silyl ($R_{21}$ is —$SiR_{31}R_{32}R_{33}$). With triethysilane and the preferred catalyst protection of the $C_{11}$-hydroxyl group is not required, see Example 3. The $\Delta^4$-3-keto (A) and $\Delta^{1,4}$-3-keto (B) steroids do not need protecting during reaction with the silylating agent.

The silylation of the $\Delta^{16}$-20-keto steroid (I) results in the production of the $\Delta^{17(20)}$-20-silyl ether (II) which can be isolated by (1) removal of the catalyst by filtration after the addition of a filtering aid, (2) removal of the solvent(s), and (3) crystallization or purification as is well known to those skilled in the art.

The $\Delta^{17(20)}$-20-silyl ether (II) is then transformed to the corresponding 17α-hydroxy-20-keto steroid (III) by peracid oxidation with a peracid of the formula RCOOOH as is well known to those skilled in the art, see J. Organometallic Chemistry 77, C19 (1974), J. Org. Chem. 40, 3427 (1975) and Tet. Letters 4319 (1974). A variety of solvents are operable such as hydrocarbons, aromatics, ethers, chlorocarbons and esters. Preferred solvents included hexane, toluene, benzene, methylene chloride, ethylene dichloride, THF, dimethoxyethane, ethyl acetate and butyl acetate. Most preferred is methylene chloride and toluene. Preferred peracids include perbenzoic, m-chloroperbenzoic and peracetic. The reaction is performed in a temperature range of about −20 to about 50° with at least one equivalent of peracid. The reaction time varies from a few minutes to several hours depending on the particular reagents and reaction conditions. When the reaction is complete, the reaction mixture is treated with a protic solvent (water, alcohol) to remove the silyl groups. The 17α-hydroxy-20-keto steroid (III) product is isolated by standard procedures well known to those skilled in the art.

The 17α-hydroxy-20-keto steroids (III) are useful as is well known to those skilled in the art.

DEFINITIONS

The definitions and explanations below are for the terms as used throughout the entire patent application including both the specification and the claims.

All temperatures are in degrees Centigrade.

TLC refers to thin-layer chromatography.

THF refers to tetrahydrofuran.

NMR refers to nuclear (proton) magnetic resonance spectroscopy, chemical shifts are reported in ppm ($\delta$) downfield from tetramethylsilane.

R is alkyl of 1 through 6 carbon atoms or phenyl substituted with 0 thru 3 substituents selected from the group consisting of alkyl of 1 thru 3 carbon atoms, chlorine or bromine.

R' is a hydrogen atom, alkyl of 1 through 6 carbon atoms, alkoxy where the alkyl group is from 1 through 3carbon atoms, phenyl, dimethylsiloxy, with the proviso that R' and R'' when both alkyl can be cyclized to give the cyclotetra- or -penta- methylene methyl silane (IV).

R'' is a hydrogen atom, alkyl of 1 through 3 carbon atoms, phenyl, dimethylsiloxy, with the proviso that R' and R'' when both alkyl can be cyclized to give the cyclotetra- or -penta- methylene methyl silane (IV).

R''' is a hydrogen atom, alkyl of 1 through 6 carbon atoms, alkoxy where the alkyl group is from 1 through 3 carbon atoms, phenyl, dimethylsiloxy, with the proviso that R' and R'' when both alkyl can be cyclized to give the cyclotetra- or -penta- methylene methyl silane (IV).

$R_6$ is a hydrogen or fluorine atom or methyl group.

$R_9$ is nothing, a hydrogen, fluorine, chlorine, bromine, or oxygen atom which makes the C ring (a) $\Delta^{9(11)}$ when $R_9$ is nothing and (b) 9β,11β-epoxide when $R_9$ and $R_{11}$ taken together are an oxygen atom.

$R_{11}$ is a hydrogen or oxygen atom, two hydrogen atoms, or α- or β- hydroxyl group or —OSiR'R''R''' or —OSiR$_{31}$R$_{32}$R$_{33}$ which makes the c-ring (a) $\Delta^{9(11)}$ when $R_{11}$ is a hydrogen atom, (b) 9β, 11β-epoxide when $R_9$ and $R_{11}$ taken together are an oxygen atom and between $C_{11}$ and $R_{11}$ is a single bond and (c) a ketone when $R_{11}$ is an oxygen atom and between $C_{11}$ and $R_{11}$ is a double bond.

$R_{21}$ is a hydrogen atom, —OCO—$R_{21}\alpha$, —O-SiR'R''R''' or —OSiR$_{31}$ R$_{32}$ R$_{33}$ group.

$R_{21}\alpha$ is a hydrogen atom, alkyl of 1 through 5 carbon atoms or phenyl.

$R_{31}$ is a hydrogen atom, alkyl of 1 through 6 carbon atoms, alkoxy where the alkyl group is from 1 through 3 carbon atoms, phenyl, dimethylsiloxy, with the proviso that R$_{31}$ and R$_{32}$ when both alkyl can be cyclized to give the cyclotetra- or -penta- methylene methyl silane (IV).

$R_{32}$ is a hydrogen atom, alkyl of 1 through 6 carbon atoms, alkoxy where the alkyl group is from 1 through 3 carbon atoms, phenyl, dimethylsiloxy, with the proviso that R$_{31}$ and R$_{32}$ when both alkyl can be cyclized to give the cyclotetra- or -penta- methylene methyl silane (IV).

$R_{33}$ is a hydrogen atom, alkyl of 1 through 6 carbon atoms, alkoxy where the alkyl group is from 1 through 3 carbon atoms, phenyl, dimethylsiloxy with the proviso that R$_{31}$ and R$_{32}$ when both alkyl can be cyclized to give the cyclotetra- or -penta- methylene methyl silane (IV).

∼ indicates that the attached group can be in either the α or β configuration.

⚊ is a single or double bond.

When the term "alkyl" of through carbon atoms is used, it means and includes isomers thereof where such exist.

When solvent pairs are used, the ratios of solvents used are volume/volume (v/v).

φ refers to a phenyl group ($C_6H_5$).

n is 0 or 1.

COD refers to 1,5-cyclooctadiene.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

EXAMPLE 1

20,21-Dihydroxypregna-4,9(11),17(20)-trien-3-one 20-triethylsilyl ether 21-acetate (IIA)

21-Hydroxypregna-4,9(11),16-triene-3,20-dione 21-acetate (IA, U. S. Pat. No. 4,216,159, Example 2, 26.7 g) methylene chloride (53.5 ml) and tris(triphenylphosphine)rhodium (I) chloride (101 mg) are mixed. Triethylsilane (15 ml) is added by a syringe to the above mixture and stirred at 43° for 4 hr. The mixture is cooled to 20°-25° and a filter aid (3.6 g) is added. The mixture is filtered, and concentrated under pressure to give a solid which is crystallized from hexane to give the title compound, NMR (CDCl$_3$) 0.71, 0.82, 0.99, 1.33, 2.08, 4.57, 5.51 and 5.73δ.

EXAMPLE 2

17α,21-Dihydroxypregna-4,9(11)-diene-3,20-dione 21-acetate (IIIA)

20,21-Dihydroxypregna-4,9(11),17(20)-trien-3-one 20-triethylsilyl ether 21-acetate (IIA, Example 1, 35 g) is dissolved in toluene (146 mml) and cooled to 0-5°. A solution of peracetic acid (40%, 14.8 ml) is added dropwise over about 3 min. and the mixture is allowed to stir at 0-5° for 2 hr. and then quenched with sulfur dioxide in methanol (2M, 8.5 ml). Triethylamine (14.9 ml) is added followed by heptane (146 ml). The slurry is filtered and the solids washed with 145 ml of heptane/toluene/methanol (44/44/12) followed by cold acetone (4×60 ml). Drying under vacuum gives the title compound, NMR (CDCl$_3$) 0.63, 1.33, 2.17, 4.97, 5.55 and 5.72δ.

EXAMPLE 3

11β,20,21-Trihydroxypregna-4,17(20)-dien-3-one 20-triethylsilyl ether 21-acetate (IIA)

Following the general procedure of Example 1 and making noncritical variations, but starting with 11β,21-dihydroxypregna-4,16-diene-3,20-dione 21-acetate [IA,-JACS 77, 1028 (1955) compound (XIIIb)] the title compound is obtained.

EXAMPLE 4

11β,17α,21-Trihydroxypregna-4-ene-3,20-dione 21-acetate (IIIA)

Following the general procedure of Example 2 and making noncritical variations, but starting with 11β,20,21-trihydroxypregna-4,17(20)-dien-3-one 20-triethylsilyl ether 21-acetate (IIA, Example 3) the title compound is obtained.

EXAMPLE 5

20,21-Dihydroxypregna-4,9(11),17(20)-trien-3-one 20-(diethoxymethyl)silyl ether 21-acetate (IIA)

21-Hydroxypregna-4,9(11),16-triene-3,20-dione 21-acetate (IA, U.S. Pat. No. 4,216,159, Example 2, 0.5 g), diethoxymethylsilane (0.39 ml) tris(trisphenylphosphine)rhodium (I) chloride (2 mg) and toluene (1 ml) are heated at 45° for 3.75 hr. On cooling to 20°-25° the solvent is removed under reduced pressure to give the title compound, NMR (CDCl$_3$) 0.20, 0.90, 1.22, 1.34, 2.10, 3.86, 4.67, 5.52 and 5.77δ.

EXAMPLE 6

17α,21-Dihydroxypregna-4,9(11)-diene-3,20-dione 21-acetate (IIIA)

Oxidation of 20,21-dihydroxypregna-4,9(11),17(20)-trien-3-one 20-(diethoxymethyl)silyl ether 21-acetate (IIA, Example 5) with peracetic acid (40%) in toluene followed by aqueous acidic work-up gives the title compound.

EXAMPLE 7

20,21-Dihydroxypregna-4,9(11),17(20)-trien-3-one 20-trimethylsilyl ether 21-acetate (IIA)

A mixture of 21-hydroxypregna-4,9(11),16-triene-3,20-dione (IA, 500 mg) trimethylsilane (1.2M, 2 ml) in toluene and tris(tri-phenylphosphine)rhodium (I) chloride (2 mg) are heated at 43° with stirring in a sealed vial for 1hr. The solvent is removed under reduced pressure to give the title compound, NMR (CDCl$_3$) 0.8, 0.88, 1.33, 2.08, 4.58, 5.27 and 5.73δ.

EXAMPLE 8

17α,21-Dihydroxypregna-4,9(11)-diene-3,20-dione 21-acetate (IIIA)

20,21-Dihydroxypregna-4,9(11),17(20)-trien-3-one 20-triethylsilylether 21-acetate (IIA, Example 1, 100 mg) is dissolved in toluene (5 ml) and stirred at 20°-25° under nitrogen. m-Chloroperbenzoic acid (42 mg) in toluene (1 ml) is added in one portion. After 2 hours potassium bicarbonate (1M, 10 ml) is added and the mixture stirred as two phases for 1 hour and let stand for an additional hour. The mixture is diluted with methanol (25 ml), and treated with sulfuric acid (50% aqueous, 4 drops). The mixture is stirred at 20°-25° for 1 hour and then poured into water (150 ml) and extracted with ethyl acetate (25 ml). The organic layer is washed with water containing sulfuric acid, dried over sodium sulfate and concentrated under vacuum to give the title compound.

EXAMPLE 9

20.21-Dihydroxypregna-4,9(11),17(20)-trien-3-one 20-(ethoxydimethyl)silyl ether 21-acetate (IIA)

Following the general procedure of Example 1 and making non-critical variations but using ethoxydimethylsilane the title compound is obtained; Rf=0.44 (starting material=0.20).

EXAMPLE 10

17α,21-Dihydroxypregna-4,9(11)-diene-3,20-dione 21-acetate (IIIA)

Following the general procedure of Example 2 and making non-criticalvariations but starting with 20,21-dihydroxypregna-4,9(11),17(20)-trien-3-one 20-ethoxydimethylsilyl ether 21-acetate (IIA, Example 9) the title compound is obtained.

EXAMPLE 11

20,21-Dihydroxypregna-4,9(11),17(20)-trien-3-one 20-(dimethylsiloxy)dimethylsilyl ether 21-acetate (IIA)

Following the general procedure of Example 1 and making non-critical variations but using tetramethyldisiloxane the title compound is obtained; Rf=0.52 (starting material=0.20).

EXAMPLE 12

17α,21-Dihydroxypregna-4,9(11)-diene-3,20-dione 21-acetate (IIIA)

Following the general procedure of Example 2 and making non-critical variations but starting with 20,21-dihydroxypregna-4,9(11),17(20)-trien-3-one 20-(dimethylsiloxy)dimethyl silyl ether 21-acetate (IIA, Example 11) the title compound is obtained.

CHART A

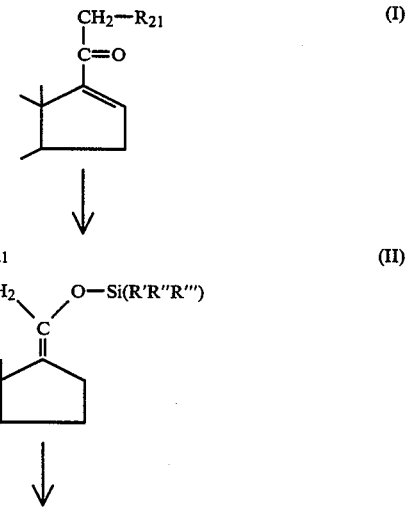

-continued
CHART A

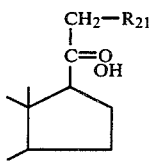
(III)

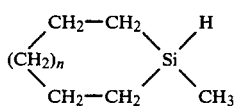
(IV)

CHART B

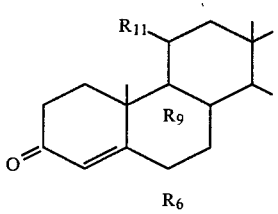
(A)

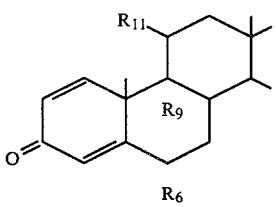
(B)

I claim:
1. A $\Delta^{17(20)}$-20-silyl ether of the formula

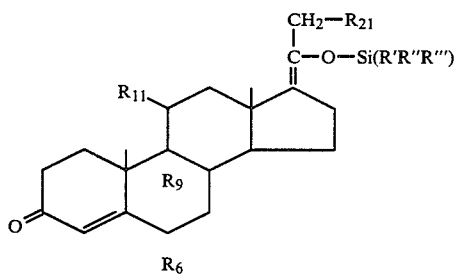
(II A-B)

where
R' is a hydrogen atom, alkyl of 1 through 6 carbon atoms, alkoxy where the alkyl group is from 1 through 3 carbon atoms, phenyl, dimethylsiloxy, with the proviso that R' and R" when both alkyl can be cyclized to give the cyclotetra- or -pentamethylene methyl silane;

R" is a hydrogen atom, alkyl of 1 through 6 carbon atoms, alkoxy where the alkyl group is from 1 through 3 carbon atoms, phenyl, dimethylsiloxy, with the proviso that R' and R" when both alkyl can be cyclized to give the cyclotetra- or -pentamethylene methyl silane;

R'" is a hydrogen atom, alkyl of 1 through 6 carbon atoms, alkoxy where the alkyl group is from 1 through 3 carbon atoms, phenyl, dimethylsiloxy, with the proviso that R' and R" when both alkyl can be cyclized to give the cyclotetra- or -pentamethylene methyl silane;

$R_6$ is a hydrogen or fluorine atom or methyl group;

$R_9$ is nothing, a hydrogen, fluorine, chlorine, bromine, or oxygen atom which makes the C ring
 (a) $\Delta^{9(11)}$ when $R_9$ is nothing and
 (b) $9\beta,11\beta$-epoxide when $R_9$ and $R_{11}$ taken together are an oxygen atom;

$R_{11}$ is a hydrogen or oxygen atom, two hydrogen atoms, $\alpha$- or $\beta$- hydroxyl group or —OSiR'R"R'" or —OSiR$_{31}$R$_{32}$R$_{33}$ which makes the C-ring
 (a) $\Delta^{9(11)}$ when $R_{11}$ is a hydrogen atom,
 (b) $9\beta,11\beta$-epoxide when $R_9$ and $R_{11}$ taken together are an oxygen atom and between $C_{11}$ and $R_{11}$ is a single bond and
 (c) a ketone when $R_{11}$ is an oxygen atom and between $C_{11}$ and $R_{11}$ is a double bond;

$R_{21}$ is a hydrogen atom, —OCO—R$_{21}\alpha$, —O-SiR'R"R'" or —OSiR$_{31}$R$_{32}$R$_{33}$ group;

$R_{21}\alpha$ is a hydrogen atom, alkyl of 1 through 5 carbon atoms or phenyl;

$R_{31}$ is a hydrogen atom, alkyl of 1 through 6 carbon atoms, alkoxy where the alkyl group is from 1 through 3 carbon atoms, phenyl, dimethylsiloxy, with the proviso that R$_{31}$ and R$_{32}$ when both alkyl can be cyclized to give the cyclotetra- or -pentamethylene methyl silane;

$R_{32}$ is a hydrogen atom, alkyl of 1 through 6 carbon atoms, alkoxy where the alkyl group is from 1 through 3 carbon atoms, phenyl, dimethylsiloxy, with the proviso that R$_{31}$ and R$_{32}$ when both alkyl can be cyclized to give the cyclotetra- or -pentamethylene methyl silane;

$R_{33}$ is a hydrogen atom, alkyl of 1 through 6 carbon atoms, alkoxy where the alkyl group is from 1 through 3 carbon atoms, phenyl, dimethysiloxy with the proviso that R$_{31}$ and R$_{32}$ when both alkyl can be cyclized to give the cyclotetra- or -pentamethylene methyl silane;

~indicates that the attached group can be in either the $\alpha$ or $\beta$ configuration;

is a single or double bond.

2. $\Delta^{17(20)}$-20-silyl ether according to claim 1 where the $\Delta^{17(20)}$-silyl ether (II) is a $\Delta^4$-3-keto steroid of the formula

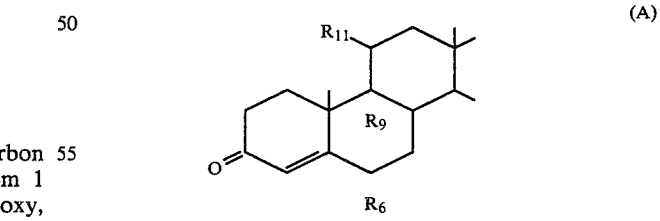
(A)

where $R_6$, $R_9$, $R_{11}$, ~and are defined in claim 1.

3. A $\Delta^{17(20)}$-20-silyl ether according to claim 1 where $R_9$ is nothing or an oxygen atom and where $R_{11}$ is a hydrogen or an oxygen atom making the C-ring $\Delta^{9(11)}$ or a $9\beta,11\beta$-epoxide.

4. A $\Delta^{17(20)}$-20-silyl ether according to claim 1 where the C-ring is $\Delta^{9(11)}$.

5. A $\Delta^{17(20)}$-20-silyl ether according to claim 1 where $R_{21}$ is —OCOR$_{21}\alpha$ and where R$_{21}\alpha$ is methyl, ethyl or phenyl.

6. A $\Delta^{17(20)}$-silyl ether according to claim 1 where R', R", R''' are the same or different and are selected from the group consisting of methyl, ethyl, methoxy, ethoxy, phenyl, and dimethylsiloxy.

7. A $\Delta^{17(20)}$-20-silyl ether according to claim 1 where the $\Delta^{17(20)}$-20-silyl ether (II) is selected from the group consisting of 20,21-dihydroxypregna-4,9(11),17(20)-trien-3-one 20-triethylsilyl ether 21-acetate; 11β,20,21-trihydroxypregna-4,17(20)-dien-3-one 20-triethylsilyl ether 21-acetate; 20,21-dihydroxypregna-4,9(11), 17(20)-trien-3-one 20-(diethoxy)methylsilyl ether 21-acetate; 20,21-dihydroxypregna-4,9(11),-17(20)-trien-3-one 20-trimethylsilyl ether 21-acetate; 20,21-dihydroxypregna-4,9(11),17(20)-trien-3-one 20-ethoxydimethylsilyl ether 21-acetate; 20,21-dihydroxypregna-4,9(11),17(20)-trien-3-one 20-(dimethylsiloxy)dimethyl silyl ether 21-acetate.

8. A process for the preparation of a 17α-hydroxy-20-keto steroid of the formula

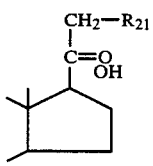

which comprises (1) contacting a Δ16-20-keto steroid of the formula

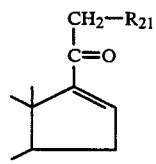

with a silylating agent of the formula R' R" R''' SiH in the presence of a transition metal catalyst to give a $\Delta^{17(20)}$-20-silyl steroid of the formula

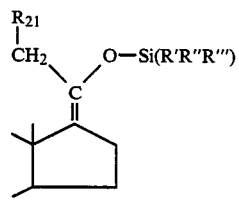

and (2) contacting the $\Delta^{17(20)}$-20-silyl steroid (II) of step (1) with a peracid where R', R", R''' and $R_{21}$ are defined in claim 1.

9. A process according to claim 8 where the $\Delta^{17(20)}$-silyl ether (II) is a $\Delta^4$-3-keto steroid of the formula

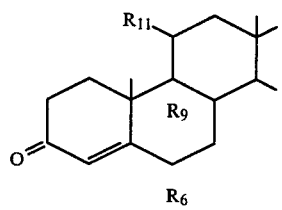

or a $\Delta^{1,4}$-3-keto steroid of the formula

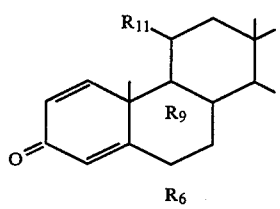

where $R_6$, $R_9$, $R_{11}$, and ∼ are defined in claim 1.

10. A process according to claim 8 where $R_9$ is nothing or an oxygen atom and where $R_{11}$ is a hydrogen or an oxygen atom making the C-ring $\Delta^{9(11)}$ or a 9β,11β-epoxide.

11. A process according to claim 8 where the C-ring is $\Delta^{9(11)}$.

12. A process according to claim 8 where $R_{21}$ is —O-$COR_{21a}$ and where $R_{21a}$ is methyl, ethyl or phenyl.

13. A process according to claim 8 where R', R", R''' of the silylating agent are the same or different and are selected from the group consisting of methyl, ethyl, methoxy, ethoxy, phenyl, and dimethylsiloxy.

14. A process according to claim 8 where the silylating agent is selected from the group consisting of trimethylsilane, triethylsilane, diethoxymethylsilane, ethoxydimethylsilane, dimethylmethoxysilane and tetramethyldisiloxane.

15. A process according to claim 8 where the transition metal catalyst is selected from the group consisting of tris(triphenylphosphine)rhodium (I) chloride, $H_2PtCl_6 \cdot H_2O$, $(\phi_3P)_2PtCl_2$, Pt(O) on supports; $PdCl_2$, $(\phi_3P)_4Pd$, $(\phi_3P)_2PdCl_2$; $(\phi_3P)_3RuCl_2$; $(\phi_3P)_2Rh(CO)Cl$, $(\phi_3P)_3Rh(CO)H$, $[RhCl(CO)]_2$, $[(C_2H_4)_2RhCl]_2$; $Co_2(CO)_8$, $HCo(CO)_4$, $(\phi_3P)_3CoH_3$; $(\phi_3P)_3NiCl_2$, $Ni(CO)_4$, and $[Ni(COD)_2]$.

16. A process according to claim 15 where the transition metal catalyst is selected from the group consisting of $(\phi_3P)_3RhCl$, $(\phi_3P)_3Rh(CO)Cl$, $(100 \ _3P)Rh(CO)Cl$, $[RhCl(CO)_2]_2$ and $[(C_2H_4)_2RhCl]_2$.

17. A process according to claim 16 where the transition metal catalyst is tris(triphenylphosphine)rhodium (I) chloride: $(\phi_3P)_3RhCl$.

18. A process according to claim 8 where the peracid is of the formula RCOOOH where R is alkyl of 1 through 6 carbon atoms or phenyl substituted with 0 thru 3 substituents selected from the group consisting of alkyl of 1 thru 3 carbon atoms, chlorine or bromine.

19. A process according to claim 18 where the peracid is selected from the group consisting of peracetic, perbenzoic and m-chloroperbenzoic.

20. A process according to claim 8 where the $\Delta^{17(20)}$-20-silyl ether (II) is selected from the group consisting of 20,21-dihydroxypregna-4,9(11),17(20)-trien-3-one 20-triethylsilyl ether 21-acetate; 11β,20,21-trihydroxypregna-4,17(20)-dien-3-one 20-triethylsilyl ether 21-acetate; 20,21-dihydroxypregna-4,9(11),17(20)-trien-3-one 20-(diethoxy)methylsilyl ether 21-acetate and 20,21-dihydroxypregna-4,9(11), 17(20)-trien-3-one 20-triemethylsilyl ether 21-acetate; 20,21-dihydroxypregna-4,9(11),-17(20)-trien-3-one 20-ethoxydimethylsilyl ether 21-acetate; 20,21-dihydroxypregna-4,9(11),17(20)-trien-3-one 20-(dimethylsiloxy)dimethyl silyl ether 21-acetate.

* * * * *

UNITED STATES PATENT OFFICE
CERTIFICATE OF CORRECTION

Patent No. 4,568,492  Dated February 4, 1986

Inventor(s) Jerry A. Walker

It is certified that error appears in the above-identified patent and that said Letters Patent are hereby corrected as shown below:

Column 3, line 30, "1 through 3 carbon atoms" should read --1 through 6 carbon atoms, alkoxy where the alkyl group is from 1 through 3 carbon atoms--
Column 3, line 51, "and      between" should read --and .... between--
Column 3, line 53, "and      between" should read --and .... between--
Column 4, line 11, "     is a single" should read --.... is a single--
Column 4, line 12, "of      through     carbon" should read --of ___ through ___ carbon--
Column 7, line 7, " 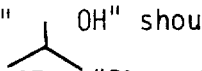 OH" should read -- 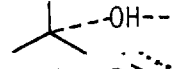 -OH--

Column 7, lines 21-27, " 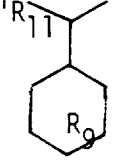 " should read -- 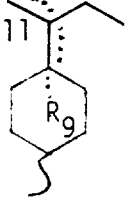 --

Column 7, lines 30-35," 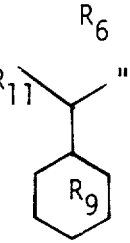 " should read -- 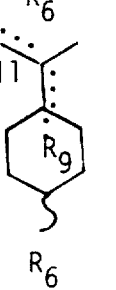 --

UNITED STATES PATENT OFFICE
CERTIFICATE OF CORRECTION

Patent No. 4,568,492                Dated February 4, 1986

Inventor(s) Jerry A. Walker

It is certified that error appears in the above-identified patent and that said Letters Patent are hereby corrected as shown below:

Column 7, lines 45-50, " 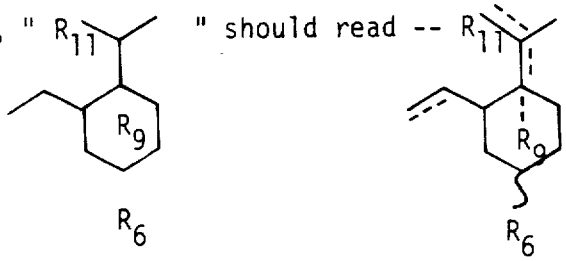 " should read --

Column 8, line 16, "and    between" should read --and .... between--
Column 8, line 18, "and    between" should read --and .... between--
Column 8, line 44, "    is a single" should read --.... is a single--
Column 8, lines 50-57, " 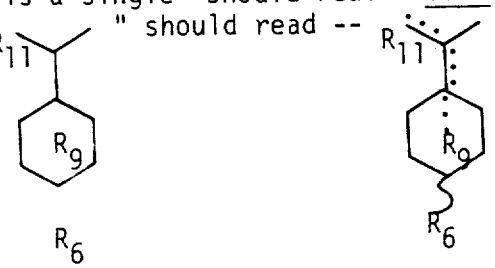 " should read --

Column 8, line 59, "and    are" should read --and .... are--
Column 9, line 30, " 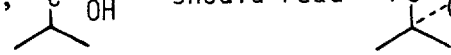 " should read --

UNITED STATES PATENT OFFICE
CERTIFICATE OF CORRECTION

Patent No. 4,568,492  Dated February 4, 1986

Inventor(s) Jerry A. Walker

It is certified that error appears in the above-identified patent and that said Letters Patent are hereby corrected as shown below:

Column 10, line 22, "$R_{11}$,          and" should read --$R_{11}$, .... and--

Signed and Sealed this

Third Day of February, 1987

Attest:

DONALD J. QUIGG

Attesting Officer   Commissioner of Patents and Trademarks